US008895033B2

(12) United States Patent
Houchin et al.

(10) Patent No.: US 8,895,033 B2
(45) Date of Patent: Nov. 25, 2014

(54) SUSTAINED RELEASE FORMULATIONS USING NON-AQUEOUS CARRIERS

(75) Inventors: Mary L. Houchin, Rockville, MD (US); Robin H. Lee, San Diego, CA (US); Hong Qi, San Diego, CA (US); Greg Oehrtman, San Diego, CA (US); Robert N. Jennings, San Diego, CA (US); Scott H. Coleman, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 379 days.

(21) Appl. No.: 13/060,225

(22) PCT Filed: Sep. 4, 2009

(86) PCT No.: PCT/US2009/056058
§ 371 (c)(1),
(2), (4) Date: May 16, 2011

(87) PCT Pub. No.: WO2010/028257
PCT Pub. Date: Mar. 11, 2010

(65) Prior Publication Data
US 2011/0212138 A1    Sep. 1, 2011

Related U.S. Application Data

(60) Provisional application No. 61/094,381, filed on Sep. 4, 2008.

(51) Int. Cl.
| A61K 9/00 | (2006.01) |
| A61K 9/51 | (2006.01) |
| A61K 38/26 | (2006.01) |
| A61K 38/28 | (2006.01) |
| A61K 38/22 | (2006.01) |
| A61K 47/14 | (2006.01) |
| A61K 31/00 | (2006.01) |
| A61K 45/06 | (2006.01) |
| A61K 9/10 | (2006.01) |
| A61K 47/44 | (2006.01) |
| A61K 31/65 | (2006.01) |
| A61K 31/60 | (2006.01) |

(52) U.S. Cl.
CPC .............. *A61K 31/00* (2013.01); *A61K 9/5153* (2013.01); *A61K 38/26* (2013.01); *A61K 38/28* (2013.01); *A61K 38/2278* (2013.01); *A61K 47/14* (2013.01); *A61K 45/06* (2013.01); *A61K 9/0019* (2013.01); *A61K 9/10* (2013.01); *A61K 47/44* (2013.01); *A61K 31/65* (2013.01); *A61K 31/60* (2013.01)
USPC ........................................................ 424/400

(58) Field of Classification Search
None
See application file for complete search history.

(56) References Cited

U.S. PATENT DOCUMENTS

| 5,213,810 | A | 5/1993 | Steber |
| 5,288,501 | A | 2/1994 | Nürnberg et al. |
| 5,288,502 | A | 2/1994 | Mcginity et al. |
| 5,439,688 | A | 8/1995 | Orsolini et al. |
| 5,556,642 | A | 9/1996 | Kobayashi et al. |
| 5,718,922 | A | 2/1998 | Herrero-Vanrell |
| 5,747,058 | A | 5/1998 | Tipton et al. |
| 5,851,451 | A | 12/1998 | Takechi et al. |
| 5,980,945 | A | 11/1999 | Ruiz |
| 6,190,700 | B1 | 2/2001 | Okada et al. |
| 6,190,702 | B1 | 2/2001 | Takada et al. |
| 6,217,893 | B1 | 4/2001 | Pellet et al. |
| 6,245,349 | B1 * | 6/2001 | Yiv et al. ............... 424/450 |
| 6,270,700 | B1 | 8/2001 | Ignatious |
| 6,277,413 | B1 | 8/2001 | Sankaram |
| 6,458,387 | B1 | 10/2002 | Scott et al. |
| 6,495,164 | B1 | 12/2002 | Ramstack et al. |
| 6,528,093 | B1 | 3/2003 | Kamei et al. |
| 6,667,061 | B2 | 12/2003 | Ramstack et al. |
| 6,899,898 | B2 | 5/2005 | Albayrak |
| 6,913,767 | B1 | 7/2005 | Cleland et al. |
| 7,163,697 | B2 | 1/2007 | Hanes et al. |
| 7,163,701 | B2 | 1/2007 | Cleland et al. |

(Continued)

FOREIGN PATENT DOCUMENTS

| EP | 1755650 B1 | 7/2008 |
| EP | 2133073 A1 | 12/2009 |

(Continued)

OTHER PUBLICATIONS

Tracy MA et al. Factors affecting the degradation rate of poly(lactide-co-glycolide) microspheres in vivo and in vitro. Biomaterials. Jun. 1999;20(11):1057-62) employing poly lactide-co glycilide.*

(Continued)

*Primary Examiner* — Robert A Wax
*Assistant Examiner* — Olga V Tcherkasskaya
(74) *Attorney, Agent, or Firm* — Womble Carlyle Sandridge & Rice, LLP

(57) ABSTRACT

The disclosure provides one-component, injectable, sustained release formulations which comprise microspheres containing active pharmaceutical ingredients (e.g., exenatide), wherein the microspheres are suspended in a non-aqueous carrier. The non-aqueous carrier can be an oil, a fractionated oil, triglycerides, diglycerides, monoglycerides, propylene glycol fatty acid diesters, and the like. The formulations offer distinct advantages of long shelf life for the stability and potency of the formulation and sustained release of active pharmaceutical ingredients to reduce the frequency of medication dosing and to increase patient compliance.

18 Claims, 7 Drawing Sheets

(56) References Cited

U.S. PATENT DOCUMENTS

| | | | |
|---|---|---|---|
| 7,252,842 B2 | 8/2007 | Albayrak | |
| 7,276,251 B2 | 10/2007 | Kim et al. | |
| 7,303,764 B2 | 12/2007 | Allen et al. | |
| 7,368,126 B2 | 5/2008 | Chen et al. | |
| 7,371,406 B2 | 5/2008 | Ramstack et al. | |
| 7,589,169 B2 * | 9/2009 | Bolotin | 530/308 |
| 7,635,463 B2 * | 12/2009 | Bolotin et al. | 424/1.65 |
| 7,790,140 B2 * | 9/2010 | Bolotin | 424/1.65 |
| 8,231,859 B2 * | 7/2012 | Bolotin et al. | 424/1.65 |
| 8,257,682 B2 * | 9/2012 | Bolotin et al. | 424/1.65 |
| 8,277,776 B2 * | 10/2012 | Bolotin et al. | 424/1.65 |
| 2004/0071785 A1 * | 4/2004 | Dulieu et al. | 424/491 |
| 2004/0224030 A1 * | 11/2004 | Shastri et al. | 424/490 |
| 2005/0260259 A1 * | 11/2005 | Bolotin | 424/450 |
| 2006/0093660 A1 * | 5/2006 | Bolotin | 424/450 |
| 2006/0099256 A1 | 5/2006 | Price et al. | |
| 2006/0146490 A1 * | 7/2006 | Chen et al. | 361/683 |
| 2006/0210614 A1 * | 9/2006 | Quay et al. | 424/448 |
| 2008/0145439 A1 * | 6/2008 | Lobl et al. | 424/498 |
| 2008/0146490 A1 * | 6/2008 | Joabsson et al. | 514/2 |
| 2011/0263496 A1 | 10/2011 | Fineman et al. | |
| 2013/0172250 A1 | 7/2013 | Fineman et al. | |

FOREIGN PATENT DOCUMENTS

| | | |
|---|---|---|
| WO | WO 97/44039 | 11/1997 |
| WO | WO 98/30231 | 1/1998 |
| WO | WO 98/07412 | 2/1998 |
| WO | WO 2004036186 | 4/2004 |
| WO | WO/2005/102293 | 11/2005 |
| WO | WO 2008/021133 | 2/2008 |
| WO | WO 2008/041245 | 4/2008 |
| WO | WO 2008/133908 | 11/2008 |
| WO | WO 2009/143285 | 11/2009 |

OTHER PUBLICATIONS

Ertl HC et al. Poly (DL-lactide-co-glycolide) microspheres as carriers for peptide vaccines. Vaccine. Jun. 1996;14(9):879-85.*

Kim et al. Microspheres for Drug Delivery. in: BioMEMS and Biomedical Nanotechnology. Eds. A.P. Lee; J. Lee. (2006)vol. I:Chapter 2:19-50.*

Gedulin et al., Diabetologia 48:1380-1385 (2005): Dose-response for glycaemic and metabolic changes 28 days after single injection of long-acting release exenatide in diabetic fatty Zucker rats.

Hou et al., Yao Xue Xue Bao 40(1):57-64 (Jan. 2005) "The Stability of Insulin-Loaded Polybutylcyanoacrylate nanoparticles in an Oily Medium and the Hypoglycemic Effect in Diabetic Rats".

Jain et al., Eur. J. Pharmaceutics & Biopharmaceutics 50:257-262 (2000) "Controlled release of drugs from injectable in situ formed biodegradable PLGA microspheres: effect of various formulation variables".

Legarce et al., Eur. J. Pharmaceutics and Biopharmaceutics 61:171-180 (2005) "Baclofen-Loaded Microspheres in gel suspensions for intrathecal drug delivery: in vitro and in vivo evaluation".

Luan & Bodmeier, Eur. J. Pharmaceutics & Biopharmaceutics 63:205-214 (2006) "Modification of the tri-phasic drug release pattern of leuprolide acetate-loaded poly(lactide-co-glycolide) mcroparticles".

Porjazoska et al., Acta Pharm. 54:215-229 (2004) Poly(lactide-co-glycolide) microparticles as systems for controlled release of proteins—preparation and characterization.

Thompson et al., J. Controlled Release 43:9-22 (1997) Biodegradable microspheres as a delivery system for rismorelin porcine, a porcine-growth-hormone releasing hormone.

International Search Report PCT/US09/56058 mailed Nov. 9, 2009.

Hungarian Search Report 201101519-5, page 3 of 9, mailed Aug. 6, 2012.

* cited by examiner

SUSTAINED RELEASE FORMULATIONS USING NON-AQUEOUS CARRIERS

RELATED APPLICATIONS

This is a §371 application of PCT/US2009/056058, with an international filing date of 4 Sep. 2009, which claims benefit of priority from U.S. Ser. No. 61/094,381, filed 4 Sep. 2008, both of which are hereby incorporated by reference in their entirety, including all tables, figures and claims.

BACKGROUND

Injectable sustained release formulations offer the opportunity to provide therapeutic amounts of active pharmaceutical ingredients over an extended period of time from a single injection, thus eliminating the need for once or twice daily injections. Presently available injectable sustained release formulations utilizing, for example, microspheres and an aqueous carrier, carry several disadvantages. The formulations do not offer long term stability in the aqueous carrier, thus necessitating separate packaging and storage for the microspheres and aqueous carrier, and the patient must take several steps to combine the microspheres and aqueous carrier before administering the injection.

Another disadvantage of presently available injectable microsphere formulations is a large burst release following injection, which causes an undesirable in vivo release of active pharmaceutical ingredient in a single burst. When medications have toxic or deleterious side effects, this is undesirable.

There is a need for formulations and methods of safely administering sustained release pharmaceutical formulations to patients so that the active ingredient will be released in vivo over an extended period of time and without an unacceptable initial burst release. Ideally the active ingredient is released so as to maintain levels within the therapeutic window, i.e., in the concentration range above that needed to cause the desired clinical effect, but below that where undesirable side effects outweigh the benefits of the drug. It is also necessary that this active pharmaceutical ingredient be provided in a manner that is easy and convenient for the patient to self-administer and that is provided in a formulation that maintains stability for a long period of time in a liquid state. The disclosure is directed to these as well as other important ends.

SUMMARY

The disclosure provides formulations comprising microspheres that contain active pharmaceutical ingredients, where the microspheres are suspended in a non-aqueous pharmaceutically acceptable carrier. The formulations are one-component injectable microsphere formulations, such that they do not require the patient to mix the formulation with a pharmaceutically acceptable carrier prior to injection. The disclosure offers distinct advantages over prior two-component formulations by providing for a long shelf life of the composition in the carrier, sustained release of the active pharmaceutical ingredient, a less complex carrier, a more easily manufactured carrier, a less complex injection-delivery apparatus, a kit with less components, and ease of use by patients.

The disclosure provides sustained release formulations comprising a pharmaceutically acceptable carrier which consists essentially of one or more triglycerides which comprise $C_6$-$C_{12}$ fatty acids; and microspheres which consist essentially of a poly(lactide-co-glycolide) polymer having dispersed therein about 1% to 10% (w/w) exenatide and about 0.1% to 5% (w/w) of a sugar; wherein the ratio of lactide:glycolide in the polymer is about 70:30 to 30:70, or about 1:1. In one embodiment, the exenatide is present in an amount of 1% to 5% (w/w) or 5% (w/w) and the sugar is present in an amount of 2% (w/w). The sugar may be, e.g., glucose, dextrose, galactose, maltose, fructose, mannose, sucrose, lactose, trehalose, raffinose, acarbose, glycol, glycerol, erythritol, threitol, arabitol, ribitol, sorbitol, dulcitol, iditol, isomalt, maltitol, lactitol, mannitol, xylitol, or a combination of two or more thereof. In one embodiment, the sugar is sucrose. The formulation is a suspension whereby the microspheres are suspended in the carrier. In one embodiment, the total pore volume of the microspheres is about 0.1 mL/g or less, as determined using mercury intrusion porosimetry, to provide a release profile having a ratio of maximum serum concentration of exenatide during the period of release ($C_{max}$) to average serum concentration of exenatide during the period of release ($C_{ave}$) of about 3 or less. Further, although the microspheres are formulated in oil (i.e. a carrier as disclosed herein), the microspheres do not necessarily have oil contained within the interior spaces or pores, or within a substantial number of interior spaces or pores, of the microspheres, and yet can achieve the surprising properties disclosed herein.

The disclosure provides sustained release formulations comprising a pharmaceutically acceptable non-aqueous carrier and microspheres which comprise a biocompatible, biodegradable polymer and an active pharmaceutical ingredient. In one embodiment, the total pore volume of the microspheres is about 0.1 mL/g or less, as determined using mercury intrusion porosimetry, to provide a release profile having a ratio of maximum serum concentration of the active pharmaceutical ingredient during the period of release ($C_{max}$) to average serum concentration of the active pharmaceutical ingredient during the period of release ($C_{ave}$) of about 3 or less. Further, although the microspheres are formulated in oil (i.e. a carrier as disclosed herein), in some embodiments the microspheres do not have oil contained within the interior spaces or pores, or do not have oil within a substantial number of interior spaces or pores of the microspheres, and yet can achieve the surprising properties disclosed herein. The formulation is a suspension whereby the microspheres are suspended in the carrier. The non-aqueous carrier may be an oil, such as fractionated oils, triglycerides, diglycerides, monoglycerides, propylene glycol fatty acid diesters, and the like.

In one embodiment the active ingredient is not soluble in the carrier. In various other embodiments the active ingredient has a solubility in the carrier of less than 0.01 mg/ml, or less than 0.05 mg/ml or less than 0.1 mg/ml or less than 0.5 mg/ml or less than 1 mg/ml. In still other embodiments the active pharmaceutical ingredient has a solubility in the carrier such that less than 10% of the active ingredient in the formulation is contained within the carrier with the remaining 90% contained within the microparticles. In further embodiments less than 5% or less than 2% or less than 1% or less than 0.5% of the active ingredient is contained in the carrier. In still further embodiments where it is desirable to have some active ingredient immediately available, it may also be directly incorporated into the carrier in a pharmaceutically effective amount.

The disclosure provides a kit, available to a patient or medical service provider. The kit contains a container having a formulation of the invention, and instructions for use. In one embodiment the container is a pen injector. The pen injector can be a single-dose pen injector or a multi-dose pen injector. In one embodiment the container is a vial, which can be either a single-dose vial or a multi-dose vial. In another embodiment the container is a cartridge, such as a cartridge for use in a injection apparatus. The cartridge can be either a single-dose or a multi-dose cartridge. In different embodiments the kit contains 1, 2, 3, 4, or even 5 or more such containers carrying a formulation of the invention. One further advantage of the formulations is that in one embodiment the container is provided preservative free. But in other embodiments a preservative can be soluble in the selected carrier and provided in the formulation.

BRIEF DESCRIPTION OF THE DRAWINGS

For each of FIGS. 1-6, the microspheres comprise a poly (lactide-co-glycolide) copolymer having exenatide dispersed therein, as described in Example 1. For each of FIGS. 2-6, the oil carrier is a medium chain triglyceride (MCT) commercially available as MIGLYOL® 812 (Sasol Germany GmbH, Witten, Germany).

In FIG. 5A, the purity of exenatide was determined by strong cation exchange HPLC.

DETAILED DESCRIPTION

Figure 1:
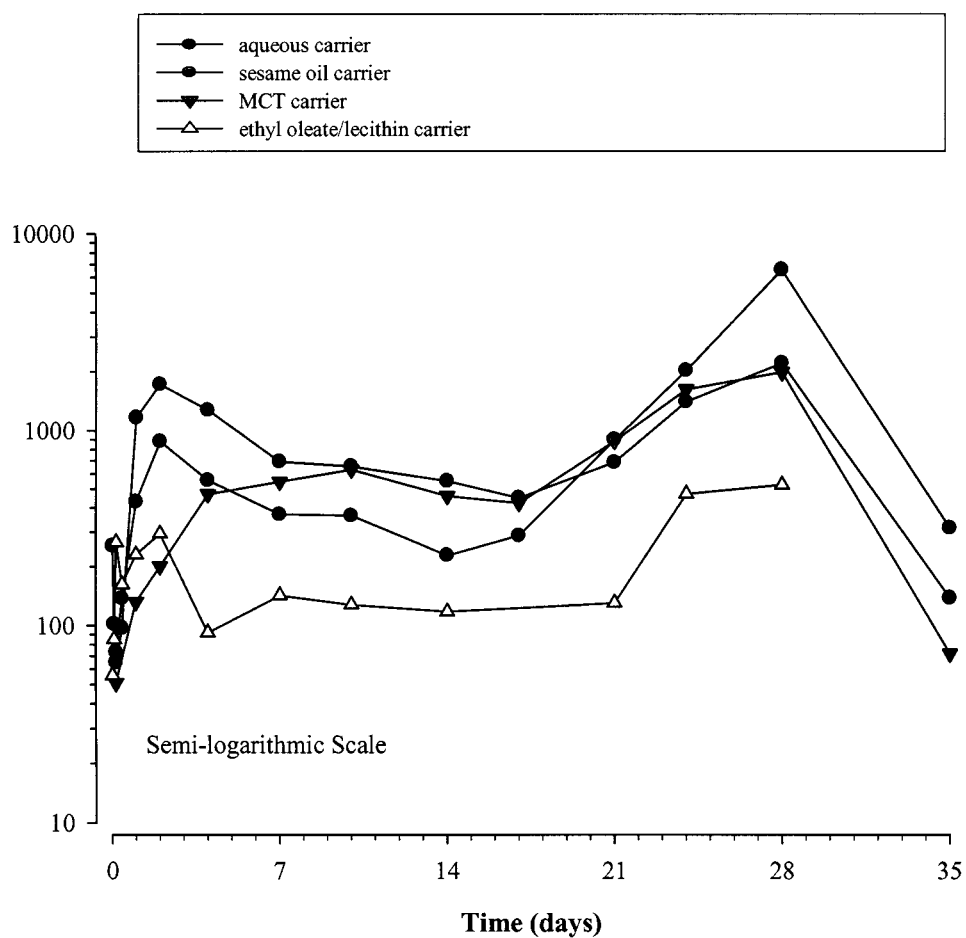
FIG. 1 provides a comparison of the pharmacokinetics of four different formulations of microspheres. In three formulations, the carrier was an oil (e.g., sesame oil; MIGLYOL® 812; ethyl oleate). In the comparative formulation, the carrier was an aqueous diluent.

The disclosure provides sustained release compositions provided in pharmaceutically acceptable carriers, for the sustained release of an active pharmaceutical ingredient (API). The formulations may comprise microspheres comprised of a biocompatible, biodegradable polymer having an active pharmaceutical ingredient dispersed therein, where the microspheres are suspended in a non-aqueous carrier. The formulations are one-component injectable formulations, compared to two-component formulations which require that the microspheres be stored dry in one container while the liquid carrier can be stored in a separate container, such that the patient must mix the two together prior to injection. The formulations offer the convenience of long term stability of a pharmaceutical composition in a non-aqueous liquid carrier, thus eliminating any need for the patient to add a pharmaceutically acceptable carrier to the pharmaceutical composition prior to injection. The formulations are provided in a single container for easy use by the patient, who only need to lightly agitate the formulation before injecting it from the same container. When the container provided is also an injection device, even the step of syringing the formulation is eliminated. The formulations described herein offer the additional important advantage of substantially reducing burst release of the active pharmaceutical ingredient. Thus, even active pharmaceutical ingredients that have a toxic effect at higher concentrations can be safely administered using the formulations described herein.

The term "patient" refers to mammals, including humans, animal pets, farm animals, zoo animals, and the like. In one embodiment, the patient is a human.

The terms "treating" or "treatment" refer to the administration of one or more active pharmaceutical ingredients to a patient who has a condition or disorder or a predisposition toward a condition or disorder, with the purpose to alleviate, relieve, remedy, ameliorate, improve, slow or stop the progression or worsening of the disease, or at least one symptom of the disease, condition or disorder, or the predisposition toward the condition or disorder.

"Exenatide" has the same meaning and amino acid sequence as exendin-4. More particularly, exenatide is a synthetic peptide with the same amino acid sequence as exendin-4, which is a peptide isolated from the venom of the Gila monster.

One Component Formulation

Previous injectable formulations contained at least two components. The first component may be dry microspheres and the second component may be an aqueous pharmaceutically acceptable carrier. The first component and second component are stored in separate sealed containers (e.g., vials, injection pen chambers). The patient receives the two-component formulation, and the patient or pharmacist must physically mix the two components together prior to injection. In the case of an injection pen, the two components are mixed together immediately prior to injection into the patient. Two-component formulations typically are administered to the patient within a short time after being mixed with the pharmaceutically acceptable carrier. For example, the microsphere component and the pharmaceutically acceptable aqueous carrier are mixed together and then the formulation is administered to the patient within about 30 or 60 minutes.

The formulations described herein are one component injectable formulations. A one component injectable formulation refers to a formulation that contains both the microspheres and the pharmaceutically acceptable carrier provided in the same container, and that may be administered to the patient without the need to first combine the microspheres and the pharmaceutically acceptable carrier. Accordingly, the one component formulation is manufactured as a pre-mixed formulation for injection. A one-component formulation provides significant convenience for manufacturing, transport, storage, and patient use.

In another embodiment the one-component formulation described herein is provided in a sealed container. A "sealed container" is a container that has not been opened, punctured, or had anything introduced into it since its time of completion of manufacture. The time of completion of manufacture is the time when the container holding the formulation is initially sealed. Containers may include vials (single use or multi-use), syringes, injection pens (e.g., single use or multi-use), and the like.

Carrier

"Carrier" (or vehicle) refers to a pharmaceutically acceptable non-aqueous liquid material. The carrier is substantially inert so that it does not interact with the microspheres described herein and is non-toxic so that it does not negatively impact the patient. The carrier is preferably approved by or is awaiting approval by a regulatory agency of the Federal or a state government or listed in the U.S. Pharmacopoeia or other generally recognized pharmacopoeia for use in mammals, such as humans. The term "carrier" may include one or more compounds. The carrier is a non-solubilizing carrier, in that the carrier does not solubilize the polymer(s) that forms the microspheres. In a further embodiment, the carrier does not solubilize the active pharmaceutical ingredient(s) within the microspheres. For example, the carrier will not solubilize exenatide or other water-soluble therapeutic peptides or proteins.

The term "non-aqueous" does not exclude trace amounts of residual water that do not have a demonstrated negative impact on the stability of the sustained release compositions. Thus, a composition may have about 0.1% (w/v) water or even about 0.25% water or less than 0.1% (w/v) water or less than 0.25% (w/v) water and still be considered non-aqueous. The carrier does not solubilize the microspheres to the extent of having a demonstrated negative impact on the stability of the microspheres or demonstrated loss of burst release control. In one embodiment, the carrier does not enter or permeate the biocompatible, biodegradable polymer and is not dispersed within the biocompatible, biodegradable polymer. The carrier also does not cause swelling of the microspheres to an extent that has a demonstrated negative impact on the stability of the microspheres. For example swelling may occur to a degree of less than 1% and still be considered a non-aqueous carrier that is non-swelling of the microspheres.

In one embodiment, the non-aqueous carrier is a pharmaceutically acceptable oil. An oil is a substance that is in a viscous liquid state at ambient temperatures or slightly warmer, and is both hydrophobic (immiscible with water) and lipophilic (miscible with other oils, literally). Exemplary pharmaceutically acceptable oil carriers include vegetable oils and volatile essential oils. Exemplary pharmaceutically acceptable oil carriers include coconut oil, palm oil, palm kernel oil, sesame oil, soybean oil, almond oil, rapeseed oil, corn oil, sunflower oil, peanut oil, olive oil, castor oil, soybean oil, safflower oil, cottonseed oil, ethyl oleate, and the like. The carrier may comprise one oil or a combination of two or more oils.

In one embodiment, the carrier is a fractionated oil or a combination of two or more fractionated oils. Exemplary pharmaceutically acceptable oil carriers include fractionated coconut oil, fractionated palm oil, fractionated palm kernel oil, fractionated sesame oil, fractionated soybean oil, fractionated almond oil, fractionated rapeseed oil, fractionated corn oil, fractionated sunflower oil, fractionated peanut oil, fractionated olive oil, fractionated castor oil, fractionated soybean oil, fractionated safflower oil, fractionated cottonseed oil, and the like. In one embodiment, the carrier is fractionated coconut oil. In one embodiment, the carrier is fractionated palm kernel oil. In one embodiment, the carrier is a combination of fractionated coconut oil and fractionated palm kernel oil.

As used herein, fractionation is a process whereby long chain fatty acids are removed from the oil, such that the resulting fractionated oil substantially comprises medium chain triglycerides. The skilled artisan will appreciate that some long-chain fatty acids may remain in the fractionated oil, but generally in amounts less than 5 wt % or less than 2 wt % of the total fatty acid content of the fractionated oil.

In one embodiment, the carrier is a long chain triglyceride, a medium chain triglyceride, a diglyceride, a monoglyceride, a propylene glycol fatty acid diester, or a combination of two or more thereof.

In one embodiment, the carrier is a medium chain triglyceride. The medium chain triglyceride may be synthetic or natural (e.g., produced from fractionated oils, such as coconut oil and/or palm kernel oil). "Medium chain triglyceride" refers to esters of glycerol having three $C_6$ to $C_{12}$ fatty acid chains, where the three fatty acid chains may be the same or different. Medium chain triglycerides are represented by the compound of Formula (I):

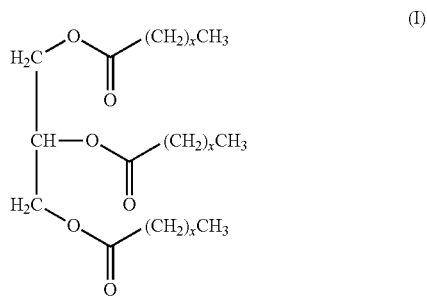

wherein each x is independently 4, 6, 8, or 10. When x is 4, the chain is referred to as a $C_6$ fatty acid. When x is 6, the chain is referred to as a $C_8$ fatty acid. When x is 8, the chain is referred to as a $C_{10}$ fatty acid. When x is 10, the chain is referred to as a $C_{12}$ fatty acid. In various embodiments, each x is the same integer; two x are the same integer and one x is a different integer; or each x is a different integer.

In various embodiment, the medium chain triglyceride comprises esters of (i) three $C_8$ fatty acids; (ii) three $C_{10}$ fatty acids; (iii) two $C_8$ fatty acids and one $C_{10}$ fatty acid; (iv) two $C_{10}$ fatty acids and one $C_8$ fatty acid; (v) two $C_8$ fatty acids and one $C_6$ fatty acid; (vi) two $C_{10}$ fatty acids and one $C_6$ fatty acid; (vii) one $C_8$ fatty acid, one $C_{10}$ fatty acid, and one $C_6$ fatty acid; or (viii) any other combination of $C_6$, $C_8$, $C_{10}$, and $C_{12}$ fatty acids. In one embodiment, the medium chain triglyceride comprises two $C_8$ fatty acids and one $C_{10}$ fatty acid. In one embodiment, the medium chain triglyceride comprises two $C_{10}$ fatty acids and one $C_8$ fatty acid.

The skilled artisan will appreciate that a mixture of medium chain triglycerides may result from any process (e.g., fractionation, hydrogenation) used to prepare medium chain triglycerides. For example, substantially all of the medium chain triglycerides obtained from fractionated coconut oil may comprise $C_8$ and/or $C_{10}$ fatty acids; however, there may be some medium chain triglycerides containing $C_6$ and/or $C_{12}$ fatty acids.

In one embodiment, the medium chain triglycerides comprise esters of (i) 0 to 2 wt % $C_6$ fatty acid, 65 to 80 wt % $C_8$ fatty acid, 20 to 35 wt % $C_{10}$ fatty acid, and 0 to 2 wt % $C_{12}$ fatty acid; (ii) 0 to 2 wt % $C_6$ fatty acid, 50 to 65 wt % $C_8$ fatty acid, 30 to 45 wt % $C_{10}$ fatty acid, and 0 to 2 wt % $C_{12}$ fatty acid; (iii) 0 to 2 wt % $C_6$ fatty acid, 45 to 65 wt % $C_8$ fatty acid, 30 to 45 wt % $C_{10}$ fatty acid, 0 to 3 wt % $C_{12}$ fatty acid; and 0 to 5 wt % linoleic acid; or (iv) 0 to 2 wt % $C_6$ fatty acid, 45 to 55 wt % $C_8$ fatty acid, 30 to 40 wt % $C_{10}$ fatty acid, 0 to 3 wt % $C_{12}$ fatty acid, and 10 to 20 succinic. In one embodiment, the medium chain triglyceride comprises 0 to 2 wt % $C_6$ fatty acid, 50 to 65 wt % $C_8$ fatty acid, 30 to 45 wt % $C_{10}$ fatty acid, and 0 to 2 wt % $C_{12}$ fatty acid, and which is commercially available as MIGLYOL® 812 (Sasol Germany GmbH, Witten, Germany) The weight % is based of the total fatty acid content of the triglycerides. In one embodiment, the medium chain triglycerides may comprise up to 2% $C_{14}$ fatty acids.

The carrier may comprise one, two, three, four or more different medium chain triglycerides. In one embodiment, the carrier comprises a medium chain triglyceride comprising esters of two $C_8$ fatty acids and one $C_{10}$ fatty acid. In one embodiment, the carrier comprises a medium chain triglyceride comprising esters of one $C_8$ fatty acid and two $C_{10}$ fatty acids. In one embodiment, the carrier comprises two different medium chain triglycerides, where a first medium chain triglyceride comprises esters of two $C_8$ fatty acids and one $C_{10}$ fatty acid and a second medium chain triglyceride comprises esters of one $C_8$ fatty acid and two $C_{10}$ fatty acids. In one embodiment, the carrier comprises a medium chain triglyceride which comprises 0 to 2 wt % $C_6$ fatty acid, 50 to 65 wt % $C_8$ fatty acid, 30 to 45 wt % $C_{10}$ fatty acid, 0 to 2 wt % $C_{12}$ fatty acid, based on the total fatty acid content of the medium chain triglyceride.

The triglycerides may be prepared by methods known in the art and are commercially available as MIGLYOL® 810, 812, 818, 829 (Sasol Germany GmbH, Witten, Germany) or NEOBEE® 1053, 895, M-5 (Stepan Company, Northfield, Ill.).

In another embodiment the carrier is a propylene glycol diester of saturated vegetable fatty acids with chain lengths of $C_8$ and $C_{10}$ (caprylic and capric acid). An example of one such commercially available carrier is MIGLYOL® 840 (Sasol Germany GmbH, Witten, Germany). The pharmaceutically acceptable, non-aqueous carrier may optionally comprise other pharmaceutically acceptable excipients. Exemplary excipients include sugars (e.g., sucrose, glucose, dextrose, galactose, maltose, trehalose, fructose, maltodextrin); sugar alcohols (e.g., glycol, glycerol, erythritol, threitol, arabitol, ribitol, sorbitol, dulcitol, iditol, isomalt, maltitol, lactitol, mannitol, xylitol); preservatives (e.g., benzoic acid, sorbic acid, meta cresol, sodium benzoate, potassium sorbate, methylparaben, propylparaben, butylparaben, benzalkonium chloride, and the like, generally oil-soluble, with some solubility in the selected carrier); and antioxidants (e.g., sodium metabisulfite, butylated hydroxy anisole, butylated hydroxy toluene, sodium sulfite, tocopherol, thymol, ascorbate, propyl gallate, and the like). In one embodiment, the carrier optionally comprises mannitol, maltodextrin, sorbitol, or a combination of two or more thereof.

The pharmaceutically acceptable carrier may contain a gel-forming agent; however, the gel-forming agent may only be present in an amount that does not cause a gel-depot to form at the site of in vivo administration of the formulation. In one embodiment, the pharmaceutically acceptable carrier does not contain a gel-forming agent. Exemplary gel-forming agents include cellulose derivatives (e.g., hydroxypropyl cellulose, carboxymethyl cellulose, hydroxyethyl cellulose, hydroxypropyl methyl cellulose, methylcellulose); polyoxyethylene and polyoxypropylene polymers or co-polymers (poloxamers); chitosan acid, and the like. The skilled artisan will understand that the formation of gels in vivo can be determined by methods known in the art, such as the use of histological sections and colored dyes.

In certain embodiments the non-aqueous, non-solubilizing carrier has a viscosity of from 5 cP to 200 cP or from 10 cP to 90 cP. In other embodiments the viscosity of the non-aqueous, non-solubilizing carrier is from 20 cP to 80 cP or from 30 cP to 70 cP. Thus, with reference to this disclosure the person of ordinary skill will be able to identify other oils, triglycerides, or non-aqueous compounds that also can be present in the non-aqueous, non-solubilizing carrier.

Microspheres

The term "microspheres" includes microspheres, microparticles, nanoparticles, pellets, cylinders, rods, discs, and the like. A microsphere can have a spherical, non-spherical or irregular shape. The microsphere will be of a size suitable for injection. A typical size range for microspheres is 1000 microns or less. In a particular embodiment, the microsphere ranges from about one to about 180 microns in diameter. In yet further embodiments suitable release profiles are obtained when microspheres range from about 1 to 100 microns, from about 30 to 90 microns, or from about 50 to 70 microns. In one embodiment the mean microsphere size is not less than or is equal to about 50, 60 or 70 microns, and preferably less than about 80, 90, or 100 microns. At larger sizes, microsphere are preferably substantially non-aggregated to allow passage through a 25 gauge needle, or a 27 gauge needle, or a 30 gauge needle, or a 31 gauge needle.

Consistent and superior release profiles are obtained by controlling size distribution. In one embodiment a mean microsphere size is about 50 microns and the lower and upper range of microsphere are about 30 and 90 microns, respectively. Distribution of microspheres can be described using a mean diameter of the volume. Mean diameter of the volume distribution represents the center of gravity of the distribution and is a type of "average particle size." In various embodiments, the microspheres have a mean diameter of the volume distribution of about 50 to 70 microns, about 50 to 60 microns or about 50, 60 or 70 microns, with a Distribution of Volume (DV) of less than or about 5%, 10%, or 15% at 30 microns and a DV of greater than or about 80%, 85%, 90% or 95% at 90 microns. In one embodiment, the microspheres have a mean diameter of the volume distribution of about 60 microns, with a Distribution of Volume (DV) of less than or about 10% at 30 microns and a DV of greater than or about 90% at 90 microns.

Microspheres may be prepared by processes known in the art and described, e.g., in U.S. Pat. Nos. 7,563,871, 7,456,254, 7,223,440, 6,824,822, 6,667,061, 6,495,164, and 6,479,065, the disclosures of which are incorporated by reference herein.

In a further embodiment, the microspheres have a less porous outer layer, and further can have a non-porous outer layer. Accordingly, in the formulations disclosed herein the oil does not have access to the interior spaces or pores or even to a substantial portion of the interior spaces or pores. It is specifically, contemplated that for each of the formulations disclosed herein the microspheres can additionally lack oil (or a carrier as disclosed herein) in the interior spaces of the microspheres. Thus, the advantages of the present formulations can be achieved without the presence of oil in the interior spaces of the microspheres when formulated.

Polymers

The microspheres comprise biocompatible, biodegradable polymers. A polymer is biocompatible if the polymer and any degradation products of the polymer are non-toxic to the patient at administered levels and also possess no demonstrated deleterious or untoward effects on the patient's body, for example a substantial immunological reaction at the injection site. Biodegradable means the polymer will degrade or erode in vivo to form smaller units or chemical species. Degradation can result, for example, by enzymatic, chemical and physical processes.

Exemplary biocompatible, biodegradable polymers include, for example, polylactides, polyglycolides, poly(lactide-co-glycolides), polylactic acids, polyglycolic acids, poly(lactic acid-co-glycolic acid)s, polycaprolactones, polycarbonates, polyesteramides, polyanhydrides, polyamino acids, polyorthoesters, polycyanoacrylates, poly(p-dioxanone), polyalkylene oxalates, biodegradable polyurethanes, blends thereof and copolymers thereof. Acceptable molecular weights for the biocompatible, biodegradable polymers can be determined by a person of ordinary skill in the art taking into consideration factors such as the desired polymer degradation rate, physical properties such as mechanical strength, end group chemistry and rate of dissolution of polymer. Typically, an acceptable range of molecular weight is of about 2,000 Daltons to about 2,000,000 Daltons. The biocompatible, biodegradable polymer can also be selected based upon the polymer's inherent viscosity. Suitable inherent viscosities are about 0.06 to 1.0 dL/g; about 0.2 to 0.6 dL/g; or about 0.3 to 0.5 dL/g.

In one embodiment, the biocompatible, biodegradable polymer is a poly(lactide-co-glycolide) copolymer (also referred to as "PLGA") having a lactide:glycolide ratio from 70:30 to 30:70, or from 60:40 to 40:60 or about 50:50. The molecular weight of the poly(lactide-co-glycolide) copolymer is about 10,000 Daltons to about 90,000 Daltons. In another embodiment, the molecular weight of the poly(lactide-co-glycolide) copolymer is about 30,000 Daltons to about 70,000, or from about 50,000 to about 60,000 Daltons.

The formulation may contain microspheres at a concentration of from 1 mg/ml to 500 mg/ml; from 25 mg/ml to 300 mg/ml; or from 50 mg/ml to 200 mg/ml.

Active Pharmaceutical Ingredient

An active pharmaceutical ingredient is a biologically active compound that has a therapeutic, prophylactic, or other beneficial pharmacological and/or physiological effect on the patient. The active pharmaceutical ingredient can also be a mixture of two or more compounds. The term "peptide" refers to any compound having two or more consecutive amino acids. As used herein, the term "peptide" is synonymous with peptide, polypeptide, and protein. In one embodiment, the peptide has a molecular weight of from 500 Da to 100 kDa; from 1 kDa to 80 kDa; from 1 kDa to 50 kDa; from 1 kDa to 30 kDa; or from 1 kDa to 20 kDa. In one embodiment, the peptide comprises 2 to 500 amino acid residues; 2 to 250 amino acid residues; 5 to 100 amino acid residues; or 5 to 50 amino acid residues.

In one embodiment, the active pharmaceutical ingredient is a GLP-1 receptor agonist compound, such as an exendin, an exendin analog, GLP-1(7-37), a GLP-1(7-37) analog, and the like. Exemplary GLP-1 receptor agonist compounds include exendin-3, exenatide, GLP-1(1-37), GLP-1(7-37)-NH$_2$, GLP-1(7-36), GLP-1(7-36)-NH$_2$, Leu$^{14}$-exendin-4, Leu$^{14}$, Phe$^{25}$-exendin-4, exendin-4(1-28), Leu$^{14}$-exendin-4(1-28), Leu$^{14}$, Phe$^{25}$-exendin-4(1-28), exendin-4(1-30), Leu$^{14}$-exendin-4(1-30), Leu$^{14}$, Phe$^{25}$-exendin-4(1-30), liraglutide, and the compounds described in, e.g., U.S. Pat. No. 7,157,555, U.S. Pat. No. 7,220,721, U.S. Pat. No. 7,223,725, and WO 2007/139941, the disclosures of which are incorporated herein by reference.

Other peptides known in the art can be used as the active pharmaceutical ingredient in the formulations described herein. Exemplary peptides include amylin, amylin agonists (e.g., pramlintide, davalintide, Val$^{27}$-davalintide); leptin, leptin agonists (e.g., metreleptin); PYY(3-36) and agonist analogs thereof; glucagon, glucagon agonists, glucagon antagonists, peptide chimera of GLP-1 receptor agonists and glucagon agonists, peptide chimera of human amylin and salmon calcitonin, insulin, heparin, low-molecular weight heparin, angiotensin, argipressin, argireline, atosiban, bivalirudin, cetrorelix, desmopressin, enfuvirtide, deptifibatide, GHRP-2, GHRP-6, gonadorelin, leuprolide, lysipressin, melanotan, nesiritide, octreotide, oxytocin, PT141, calcitonin, sermorelin, somatostatin, terlipressin, thymopentin, thymosin a1, triptorelin, vapreotide, elcatonin, ziconotide, ghrelin, nafarelin, BNP-32, and the like.

The active pharmaceutical ingredient can also be a small molecule. A "small molecule" is an organic molecule. Exemplary small molecules include metformin, sulfonylureas, TZDs, statins (e.g., atorvastatin, cerivastatin, fluvastatin, Lovastatin. mevastatin, pitavastatin, pravastatin, rosuvastatin, simvastatin); non-selective beta blockers and/or alpha-1 blockers (e.g., carvedilol, dilatrend, eucardic, carloc); PDE3 inhibitors (e.g., cilostazol); antiplatelet drugs, antithrombotic drugs, anticoagulant drugs, glycoprotein IIb/IIIa inhibitors (e.g., abciximab, eptifibatide, tirofiban); antibacterial drugs (e.g., ciprofloxacin, norfloxacin, levofloxacin, moxifloxacin, sparfloxacin, gemifloxacin, ecinofloxacin, delafloxacin); Factor Xa inhibitors (e.g., glycosaminoglycans, oligosaccharides, heparinoid); direct Xa inhibitors (e.g., xabans); direct thrombin (II) inhibitors (e.g., hirudin, argatroban, dabigatran, melagatran, ximelagatran, defibrotide, ramatroban, antithrombin III, protein C); thrombolytic drugs (e.g., plasminogen activators, urokinase, streptokinase, serine endopiptidases); ACE inhibitors (e.g., lisinopril, aceon, acertil, armix, coverene, coverex, coversum, prestarium, prexanil, Prexum, procaptan); ADP receptor/P2Y12 inhibitors (e.g., clopidogrel, ticlopidine, prasugrel); prostaglandin analogs (e.g., beraprost, prostacyclin, iloprost, treprostinil); anticoagulants (e.g., coumarin, coumatetralyl, dicoumarol, ethyl biscoumacetate, phenprocoumon, warfarin, clorindione, diphenadione, phenindione, tioclomarol); diuretics (e.g., hydrochlorothiazide); macrolides (e.g., azithromycin, clarithromycin, dirithromycin, erythromycin, roxithromycin, telithromycin); NSAIDs and COX-3 inhibitors (e.g., celecoxib, etoricoxib, parecoxib); sulphonanilides (e.g., nimesulide), and the like.

The skilled artisan will appreciate that the formulations described herein may contain two or more peptides; two or more small molecules; or a combination of small molecules and peptides. For example, the formulation may comprise two different sets of microspheres, where one set of microspheres contain one peptide (e.g., pramlintide) and another set of microspheres contain a different peptide (e.g., metreleptin). In one embodiment, 1 to 99% of the microspheres comprise one active pharmaceutical ingredient and 99 to 1% of the microspheres comprise a different active pharmaceutical ingredient. In another embodiment 30 to 70% of the microspheres comprise one active pharmaceutical ingredient and 70 to 30% of the microspheres comprise a different active pharmaceutical ingredient. The skilled artisan will appreciate that the percentage of each type of peptide in the formulation will be determined by the relative potency of the peptides. This formulation advantageously allows high potency peptides to be combined with low potency peptides for simultaneous delivery to a patient because the low potency peptides can be provided in more microspheres and the high potency peptides can be provided in fewer microspheres in the same formulation. Exemplary combinations of peptides and/or small molecules that can be administered in different sets of microspheres and in the same formulation include: pramlintide and insulin; pramlintide and metreleptin; davalintide and metreleptin; exenatide and metreleptin; lovastatin and niacin; atorvastatin and amlodipine; simvastatin and ezetimibe; exenatide and metformin; and the like.

The formulations generally contain from about 0.01% (w/w) to about 50% (w/w) of the active pharmaceutical ingredient (based on the total weight of the composition). For example, the amount of active pharmaceutical ingredient can be from about 0.1% (w/w) to about 30% (w/w) of the total weight of the composition. The amount of active pharmaceutical ingredient will vary depending upon the desired effect, potency of the agent, the planned release levels, and the time span over which the peptide will be released. In certain embodiments, the range of loading is between about 0.1% (w/w) to about 10% (w/w), for example, from 0.5% (w/w) to about 5% (w/w), or from 1% to 5% (w/w). When the active pharmaceutical ingredient is a GLP-1 receptor agonist, suitable release profiles can be obtained when the active pharmaceutical ingredient, for example exenatide, is loaded at about 2% w/w to about 7% w/w, including at about 2% w/w/, about 3% w/w, about 4% w/w, about 5% w/w, about 6% w/w, or about 7% w/w.

Sugars

The microspheres may also comprise one or more sugars. A sugar is a monosaccharide, disaccharide or oligosaccharide or a derivative thereof. Sugar alcohols of monosaccharides are suitable derivatives of sugar. Monosaccharides include, but are not limited to, glucose, fructose and mannose. A disaccharide, as further defined herein, is a compound which upon hydrolysis yields two molecules of a monosaccharide. Suitable disaccharides include, but are not limited to, sucrose, lactose and trehalose. Suitable oligosaccharides include, but are not limited to, raffinose and acarbose. The microspheres may further comprise glucose, dextrose, galactose, maltose, fructose, mannose, sucrose, lactose, trehalose, raffinose, acarbose, glycol, glycerol, erythritol, threitol, arabitol, ribitol, sorbitol, dulcitol, iditol, isomalt, maltitol, lactitol, mannitol, xylitol, or a combination of two or more thereof. In one embodiment, the sugar is sucrose, glucose, mannose, or fructose. In one embodiment, the sugar is sucrose.

The amount of sugar present in the microspheres can range from about 0.01% (w/w) to about 50% (w/w), such as from about 0.01% (w/w) to about 10% (w/w), such as from about 0.1% (w/w) to about 5% (w/w) of the total weight of the composition. In one embodiment, about 2% (w/w) sucrose is used.

Alternatively, the amount of sugar present in the microspheres can be referred to on a weight ratio with the active pharmaceutical ingredient. For example, the active pharmaceutical ingredient and sugar can be present in a ratio from about 10:1 to about 1:10 weight:weight. In particularly preferred embodiments, the ratio of active pharmaceutical ingredient (e.g., exenatide) to sugar (e.g., sucrose) is about 3:2 (w/w), 4:2 (w/w), or 5:2 (w/w). Combinations of two or more sugars can also be used. The amount of sugar, when a combination is employed, is the same as the ranges recited above.

Sustained Release

The compositions are sustained release compositions, meaning that the active pharmaceutical ingredient contained in the compositions will be released into the patient over an extended period of time such as, for example, a period of two days, or three days, or at least two days, or at least three days, or over a period of one week, two weeks, one month, three months, or one year. The release of the active pharmaceutical ingredient is considered complete when there is no longer a therapeutic level of active pharmaceutical ingredient in the patient's body, as determined by the medical judgment of those of ordinary skill in the art.

Cmax as used herein is the maximum serum concentration of drug which occurs during the period of release which is monitored. Cave as used herein, is the average serum concentration of drug derived by dividing the area under the curve (AUC) of the release profile by the duration of the release.

In one embodiment the ratio of Cmax to Cave is about 3 or less. This profile is particularly desirable for anti-diabetic or glucoregulatory polypeptides, such as those described herein. A ratio of about 3 or less can provide a Cave in a therapeutic window while avoiding adverse drug side effects which can result from higher ratios. Further by controlling the physical aspects of the sustained release composition, as described herein, a superior desired release profile can be achieved and controlled, for example, by appropriate selection of carrier properties, such as viscosity. There is thus provided a reduced burst (i.e. initial release; e.g., Cmax at 0-1 day). In other embodiments the Cmax to Cave ratio is from about 1 to about 3, or from 1 to 3, or from about 2 to about 3, or from 2 to 3. Further, a Cmax, if present, can be shifted from the burst or initial release period into the "sustained phase" of release. In one embodiment the Cmax can occur at at least 7, 14, 21, 28, 35 or 42 days post administration and can occur at any integer day in between. In a further embodiment the Cmax occurs at about 21 to 35 days after administration, and in yet another embodiment is at about 28 to 31 days, and further at about 28 days after administration. In a further embodiment the maximal concentration of drug (e.g. plasma concentration) occurs at at least 7, 14, 21, 28, 35 or 42 days post administration and can occur at any integer day in between. In yet a further embodiment the maximal concentration of drug occurs at about 21 to 35 days after administration, particularly in the case of glucoregulatory agents such as exendin-4, GLP-1, GIP or their analogs.

Longer Shelf Life

One advantage offered by the present formulations is a longer shelf life for the formulation. It was discovered unexpectedly that sustained release compositions retain remarkable stability when stored in a non-aqueous carrier as described herein. In one embodiment the formulation has a shelf life of at least 6 months. In other embodiments the formulation has a shelf life of at least 1 year, or at least 18 months, or at least 2 years. By "shelf life" is meant the formulation can be stored or maintained for that period of time under appropriate environmental conditions while retaining at least 90% of the desired activity of the active pharmaceutical ingredient relative to the activity at initial formulation (as 100%). In another embodiment the active pharmaceutical ingredient retains at least 95%, or at least 98% or at least 99% of its desired activity as compared to its activity immediately before storage. When the formulation contains microspheres, shelf life also refers to the retention of particle size and/or morphology of the microspheres. Retention of size morphology can be determined by microscopic examination, the use of which is known to persons of ordinary skill in the art.

When formulated as disclosed herein a peptide or protein as active ingredient is less susceptible to oxidation and to hydrolysis, either chemical or proteolytic, both during storage and during its sustained release period after injection. The addition of an anti-oxidant or other stabilizer is not required in these formulations, particularly those where the carrier is a medium chain triglyceride.

Reduced Burst Release

Another advantage of the present formulations is that formulations according to the present disclosure offer a significantly reduced burst release rate compared with other formulations. When previously available injectable sustained release formulations are injected into a patient there is often a "burst" of active ingredient or agent associated with the injection. Without wanting to be bound by any specific theory, it is believed this burst is caused by that quantity of active pharmaceutical ingredient in the formulation that is not retained within the polymer that is released over time. By "burst release" is meant that quantity of active pharmaceutical ingredient released within the first 24 hours after injection. In other embodiments it is that quantity of active that is release over 1 hour, or 2 hours, or 4 hours, or 8 hours, or 12 hours after injection. In various embodiments the formulation of the invention has a burst release after injection of less than 10% or less than 5%, or less than 3%, or less than 2.5%, or less than 2%, or less than 1% or less than 0.75% or less than 0.5% or less than 0.25% or less than 0.1%. Percentages refer to the percentage of the total amount of active pharmaceutical ingredient in the injected formulation. Following injection of the formulation in the patient, the burst release may occur at any time up to about 24 hours, thereafter there may be a lag time where substantially no active pharmaceutical ingredient is released from the microspheres, and then the polymeric microspheres begin degrading and releasing the active pharmaceutical ingredient. The skilled artisan will appreciate that the time period when the burst release occurs may vary from patient to patient.

Burst can be assessed by measuring the proportion of the total area under the curve for a particular time period following administration of a drug. Area under the curve (AUC) is a well established measurement in the pharmaceutical sciences and measures the amount of drug or active ingredient that reaches the bloodstream in a set period of time. As is well known in the art, the period of time selected will varying depending on the time period the concentration of the drug in the blood is expected to be detectable or within the drug's therapeutic window. AUC is calculated by plotting the concentration of the drug in the blood, for example plasma concentrations, at various times during the selected time period and then calculating the total area under the curve obtained. In one exemplary embodiment, the area under the curve is measured for a 42 day period and using the formulations described herein, the release or burst as measured within the first 24 hours is 5% or less, 2% or less, 1.5% or less, 1% or less, or 0.5% or less of the total AUC. In another embodiment, the formulations described herein result in a burst or proportion of the AUC that is 20% or less, 15% or less, 10% or less, 5% or less, or 2% or less than that obtained when the sustained release composition is contained in a carrier in which the active pharmaceutical ingredient is soluble.

In another embodiment, the formulations described herein limit initial burst such that the upper limit of the therapeutic window for the active pharmaceutical ingredient is not exceeded. The therapeutic window is the range of concentration of active pharmaceutical ingredient in the circulation, above which the active pharmaceutical ingredient has its desired effect, but below the concentration at which the adverse effects associated with the active pharmaceutical ingredient outweigh the benefits as would be generally accepted among physicians. In one exemplary embodiment, the active pharmaceutical ingredient is an exendin, for example exenatide, or agonist analogue thereof, and administration of the formulations described do not result in a circulating level of active pharmaceutical ingredient exceeding 400 pg/ml during the first 24 hours following administration. In another exemplary embodiment the active pharmaceutical ingredient is an exendin, for example exenatide, or agonist analogue thereof, and administration of the formulations described does not result in a circulating level of active pharmaceutical ingredient exceeding 350 pg/ml during the first 24 hours following administration.

Initial burst can also be assessed by comparing circulating concentrations of the active pharmaceutical ingredient in a time period immediately following administration of the formulation with the circulating concentration of the drug in a second time period that immediately follows the first. In one embodiment, use of the formulations of the present disclosure result in circulating concentrations of active pharmaceutical ingredient during the first 24 hours following administration that do not exceed the circulating concentration during the next 24 hour period. In another embodiment, use of the formulations of the present disclosure result in average circulating concentration of active pharmaceutical ingredient during the first 24 hours following administration do not exceed the average circulating concentration during the next 24 hour period.

Methods of Storing

Another aspect provides methods of storing the sustained release formulations described herein. The methods of storing the formulations described herein may also be referred to as methods of preventing the degradation of the microspheres. By "storing" is meant that the formulation is retained for a period of time within its container without adding any additional component to the container and without removing the formulation from the container (e.g., in the manufacturing facility, during transport, in the pharmacy). The storage time will typically be the amount of time between packaging of the formulation and its use by the patient. After the storage time the formulation is administered to the patient in need thereof. "Administering" to the patient includes self-administration. The methods involve storing the sustained release formulations for a period of at least 1 week, at least 2 weeks, at least 1 month, at least 3 months, at least 1 year, at least 18 months, or at least 2 years. In some embodiments, the formulations can be stored at 5° C. or 25° C. There is minimal degradation of the microspheres when the formulations are stored for such extended periods of time.

In another embodiment the invention provides methods of maintaining the potency of (e.g., preventing the loss of biological activity) and/or purity (e.g. preventing chemical changes in the molecule) an active pharmaceutical ingredient. Thus, a peptide or protein or other API that has undergone a chemical change (e.g. oxidation) may result in a loss of purity, but may still retain its potency. The methods involve storing a microsphere comprising a active pharmaceutical ingredient in a non-aqueous carrier as described herein for a period of time, whereby the potency and/or purity of the active pharmaceutical ingredient is maintained by the microspheres and the non-aqueous carrier. In the formulations described herein, at least 80%, at least 90%; at least 95%; at least 98%; or at least 99% of the potency and/or purity of the active pharmaceutical ingredient is retained for a period of time of at least 1 week, at least 2 weeks, at least 1 month, at least 3 months, at least 1 year, at least 18 months, or at least 2 years.

Methods of Administering/Treatment

In another aspect the present invention provides methods of administering an active pharmaceutical ingredient to a patient in need thereof. The methods involve administering to the patient a formulation or composition as described herein. Any of the formulations described herein can be administered by parenteral administration, using any of the methods described herein. For example, the formulations can be administered by subcutaneous, intra-muscular, intra-peritoneal, intra-abdominal, intravenous, or any suitable manner of administration. In one embodiment, the formulations described herein are administered subcutaneously. In one embodiment the methods involve injecting the formulation without the patient performing a prior step of combining the sustained release composition with a second carrier.

In one embodiment the administration does not comprise a mixing step. A mixing step is a step where the microspheres are combined with a carrier prior to injection. In various embodiments the mixing step is a step where the microspheres are combined with a carrier within the 1 week period prior to injection in the patient. The carrier can be a non-aqueous carrier, such as those described herein. Administration of the formulation refers to the complete process of the user interacting with the formulation, including mixing, combining any ingredients forming the formulation, and the actual injection or other form of providing the formulation to the patient.

The frequency of administration can vary depending on any one or a combination of factors such as the amount of the formulation administered, the release profile of the formulation, the amount of active pharmaceutical ingredient in the formulation, and the circulating level of active pharmaceutical ingredient to be achieved. In particular embodiments, the formulations described herein can be administered once daily, once per week, once every two weeks, once a month, once every two months, once every three months, once every four months, once every six months or once per year. In one embodiment, the formulation is administered once a week. In another embodiment, the formulation is administered once a month.

When the formulations comprise a GLP-1 receptor agonist, such as GLP-1 or an analog thereof, or an exendin (e.g., exenatide) or an analog thereof, they can be used to treat numerous diseases, such as diabetes (e.g., Type 1 diabetes, Type II diabetes, gestational diabetes), impaired glucose tolerance, hyperglycemia (e.g., fasting and postprandial), obesity, overweight, non-alcoholic fatty liver disease, non-alcoholic steatohepatitis (NASH), and the like. The formulations comprising a GLP-1 receptor agonist (e.g., exenatide) will also be useful to stimulate insulin release; lower plasma glucagon; reduce food intake, reduce appetite, decrease gastric motility, delay gastric emptying, lower plasma lipid (e.g., triglycerides, cholesterol) levels, and the like. These methods of treatment are described, for example, in U.S. Pat. No. 5,424,286, U.S. Pat. No. 6,858,576, U.S. Pat. No. 6,872,700, U.S. Pat. No. 6,956,025, and U.S. Pat. No. 6,956,025, and WO 2007/022518, the disclosures of which are incorporated by reference herein.

In certain embodiments, administration of any of the formulations provided herein comprising a glucoregulatory peptide such as an exendin, e.g. exenatide, result in a 2 hour plasma glucose of less than 300 mg/dl, less than 275 mg/dl, less than 250 mg/dl, or less than 225 mg/dl. In a particular embodiment administration of any of the formulations provided herein comprising a glucoregulatory peptide such as an exendin, e.g. exenatide, results in a 2 hour plasma glucose of less than 200 mg/dl. In other embodiments, administration of any of the formulations provided herein comprising a glucoregulatory peptide such as an exendin, e.g. exenatide, results in a 2 hour plasma glucose of less than 190 mg/dl, less than 180 mg/dl, less than 170 mg/dl, less than 160 mg/dl, or less than 150 mg/dl. In certain embodiments, administration of any of the formulations provided herein comprising a glucoregulatory peptide such as an exendin, e.g. exenatide, results in a 2 hour plasma glucose less than 140 mg/dl. In further embodiments, administration of any of the formulations provided herein comprising a glucoregulatory peptide such as an exendin, e.g. exenatide, results in a venous or capillary fasting blood glucose (FBG) level of less than 200 mg/dl, less than 175 mg/dl, less than 150 mg/dl, less than 140 mg/dl, less than 130 mg/dl, less than 120 mg/dl, or less than 115 mg/dl. In one embodiment, a FBG level of less than 110 mg/dl is achieved, while in another embodiment a FBG level of less than 100 mg/dl is achieved.

In additional embodiments, administration of any of the formulations provided herein comprising a glucoregulatory peptide such as an exendin, e.g. exenatide, results in a 2 hour venous or capillary blood glucose level of less than 300 mg/dl, less than 275 mg/dl, less than 250 mg/dl, less than 225 mg/dl, or less than 200 mg/dl. In a particular embodiment administration of any of the formulations provided herein comprising a glucoregulatory peptide such as an exendin, e.g. exenatide, results in a 2 hour blood glucose level of less than 180 mg/dl. In further embodiments, administration of any of the formulations provided herein comprising a glucoregulatory peptide such as an exendin, e.g. exenatide, result in blood glucose levels of less than 170 mg/dl, less than 160 mg/dl, less than 150 mg/dl, less than 140 mg/dl, less than 130 mg/dl, or less than 120 mg/dl. In particular embodiments, administration of any of the formulations provided herein comprising a glucoregulatory peptide such as an exendin, e.g. exenatide, result in a 2 hour venous blood glucose level of less than 120 mg/dl, while in other embodiments, a 2 hour capillary blood glucose level of less than 140 mg/dl is achieved.

In one embodiment, glucose levels are average glucose levels calculated over a chosen time period. Specific examples include, but are not limited to, daily average glucose levels, weekly average glucose levels, monthly average glucose levels or yearly average glucose levels. Two hour circulating glucose levels are determined after an oral glucose tolerance test (OGTT). In the standard test, 75 g of anhydrous glucose is dissolved in 250-300 ml of water and administered over 5 minutes. In children, glucose is administered at a rate of 1.75 g/kg body weight up to a maximum of 75 grams of glucose. A baseline glucose level is obtained prior to ingestion and then typically every 30 minutes for 2 hours. For gestational diabetes, a 100 g, 3 hour test is often used.

Because glucose freely crosses the cell membrane of red blood cells, erythrocyte hemoglobin undergoes a nonenzymatic glycosylation at the amine residues. Hemoglobin A1c (HbA1c) refers to the percentage of hemoglobin molecules with glucose moieties attached to the N-terminal valines of each of the two beta-chains. Glycohemoglobin includes HbA1c along with other forms of hemoglobin where glycosylation has occurred at other amino acids. The percentage of hemoglobin molecules undergoing glycosylation is proportional to the average ambient glucose concentrations during the previous during the previous 60-90 days. HbA1c is a commonly used measure to assess the state of glycemic control in patients with diabetes.

In one embodiment, administration of any of the formulations provided herein comprising a glucoregulatory peptide such as an exendin, e.g. exenatide, results in a reduction to, maintenance of, or both of HbA1c levels of less than 8%. In another embodiment HbA1c levels are reduced to, maintained at, or both to less than 7.5%, while in yet another embodiment, HbA1c levels are reduced to, maintained at, or both at less than 7%. In further embodiments, administration of any of the formulations provided herein comprising a glucoregulatory peptide such as an exendin, e.g. exenatide, results in a reduction to or maintenance of, or both of HbA1c levels to less than 6.5%, less than 6%, less than 5.5%, less than 5% less than 4.5% or less than 4%. Thus, the compositions disclosed herein are useful in a method of reducing or maintaining HbA1c levels in the blood, the methods comprising administering a composition disclosed herein. In another embodiment, administration of any of the formulations provided herein comprising a glucoregulatory peptide such as an exendin, e.g. exenatide, results in a reduction to, maintenance of, or both of glycosylated hemoglobin levels of less than 10%. In another embodiment, glycosylated hemoglobin levels are reduced to, maintained at, or both to less than 9.5%; while in yet another embodiment, glycosylated hemoglobin levels are reduced to, maintained at, or both at less than 9%.

In further embodiments administration of any of the formulations provided herein comprising a glucoregulatory peptide such as an exendin, e.g. exenatide, results in a reduction to, or maintenance of, or both of glycosylated hemoglobin levels to less than 8.5%, less than 8%, less than 7.5%, less than 7% less than 6.5%, less than 6%, less than 5.5%, less than 5%, less than 4.5% or less than 4%. In other aspects administration of any of the formulations provided herein comprising a glucoregulatory peptide such as an exendin, e.g. exenatide, results in a lower of HbA1c by at least 0.2%, at least 0.4%, at least 0.6%, at least 0.8%, at least 1%, at least 1.2%, at least 1.4%, at least 1.6%, at least 1.8%, or at least 2%. Thus, the invention provides methods of reducing or maintaining glycosylated hemoglobin levels in the blood, the methods involving administering a composition described herein.

It should be realized that a subject in need of lowering of blood glucose is not limited to patients having diabetes mellitus, but may include any subject suffering from hyperglycemia for whatever reason including, but not limited to, injury, trauma, surgery, stroke and myocardial infarction. The amount of glucose lowering will vary with the subject in question and depend on factors such as the severity of the hyperglycemia and the severity of the disease, disorder or condition in question.

EXAMPLES

The following non-limiting examples provide further illustrations of making and using the formulations described herein, and are not intended to limit the scope of the appended claims. With respect to the Examples herein, MCT oil refers to medium chain triglyceride oil which is commercially available as MIGLYOL® 812 (Sasol Germany GmbH, Witten, Germany).

Example 1

Microspheres may be prepared by processes known in the art and described, e.g., in U.S. Pat. No. 7,563,871 and U.S. Pat. No. 7,456,254. Microspheres comprising a poly(lactide-co-glycolide) copolymer having dispersed therein 5% (w/w) exenatide and 2% (w/w) sucrose were obtained. The poly(lactide-co-glycolide) copolymer had a ratio of lactide:glycolide of 1:1. These microspheres are currently being developed by Amylin Pharmaceuticals, Inc. (San Diego, Calif.), Alkermes, Inc. (Cambridge, Mass.), and Eli Lilly and Company (Indianapolis, Ind.) for a once-weekly formulation for treating diabetes. Gedulin et al, Diabetologia, 48:1380-1385 (2004).

Example 2

The stability of the microspheres from Example 1 was investigated to determine their stability over an extended period of time while stored in a non-aqueous carrier. Microspheres from Example 1 were stored for a period of 6 months at 5° C. in a formulation comprising a non-aqueous carrier (i.e., sesame oil; MCT oil; and ethyl oleate, which is a monoglyceride). The control was an aqueous formulation comprising the microspheres from Example 1 in an aqueous carrier containing carboxymethylcellulose and a surfactant.

The stability of the microspheres was determined by morphology and particle size via examination under a microscope. Exenatide purity, potency (by HPLC evaluation), and in vitro release were also determined. As shown in Table 1, after 6 months of storage the physical structure (i.e., size, morphology) of the microspheres did not change.

As shown in Table 2, the microspheres stored in a MCT oil showed no change in the purity of exenatide based on an HPLC analysis. Impurities might also be referred to as degradation products from the peptide. High purity means relatively little degradation of the peptide. The purity is relative to the formulation at time zero. The microspheres stored in sesame oil and ethyl oleate showed a slight decrease in the purity of exenatide. The impurities did not appear to be oil or poly(lactide-co-glycolide) polymer related (based on retention times), but appeared to be related to the stability of exenatide itself.

Table 3 shows that the potency of exenatide did not significantly decrease over the 6 month period regardless of the non-aqueous carrier that was used.

TABLE 1

Particle size and morphology using microscope

| | size (μm) (standard deviation (μm)) | | | morphology |
|---|---|---|---|---|
| | T = 0 | 1 month | 6 months | 0 to 6 months |
| sesame oil | 64 (22) | 63 (23) | 64 (12) | no change |
| MCT oil | 65 (19) | 60 (22) | 61 (17) | no change |
| ethyl oleate | 64 (16) | 62 (16) | 59 (13) | no change |

TABLE 2

Change in Purity of Exenatide Containing Formulation

| | % purity of exenatide | | | | | |
|---|---|---|---|---|---|---|
| | t = 0 | 1 month | % change* | 3 month | % change* | 6 month | % change* |
| sesame oil | 95.93 | 95.68 | −0.25 | 94.55 | −1.38 | 95.00 | −0.93 |
| MCT oil | 95.63 | 95.56 | −0.07 | 94.67 | −0.96 | 95.50 | −0.13 |
| ethyl oleate | 95.60 | 95.80 | 0.20 | 93.67 | −1.93 | 94.70 | −0.90 |

*Changes less than 0.5% are considered to be insignificant

TABLE 3

Change in Potency of Exenatide Based on Carrier in Formulation

| carrier | time zero | 1 month | 3 months | 6 months |
|---|---|---|---|---|
| sesame oil | 97 | 104 | 98 | 98 |
| MCT oil | 94 | 108 | 99 | 99 |
| ethyl oleate | 95 | 98 | 99 | 100 |

Example 3

The pharmacokinetics of the formulations in Example 2 were determined, except that 2% (w/w) lecithin was added to the ethyl oleate carrier. Single injections with a dose of 53 mg/ml of microspheres per ml of non-aqueous carrier were administered to 6 rats with a 21G needle. In the study, a comparison was also made to the microspheres from Example 1 that were mixed with an aqueous carrier just before injection.

FIG. 1 provides a comparison of the pharmacokinetics of the four different formulations of microspheres containing exenatide. In three formulations, the carrier is an oil (e.g., sesame oil; MCT oil; ethyl oleate). In one comparative formulation, the carrier is an aqueous diluent. As can be seen from the data, the formulations having an oil carrier had reduced burst when compared to the formulation having an aqueous carrier.

Figure 2:
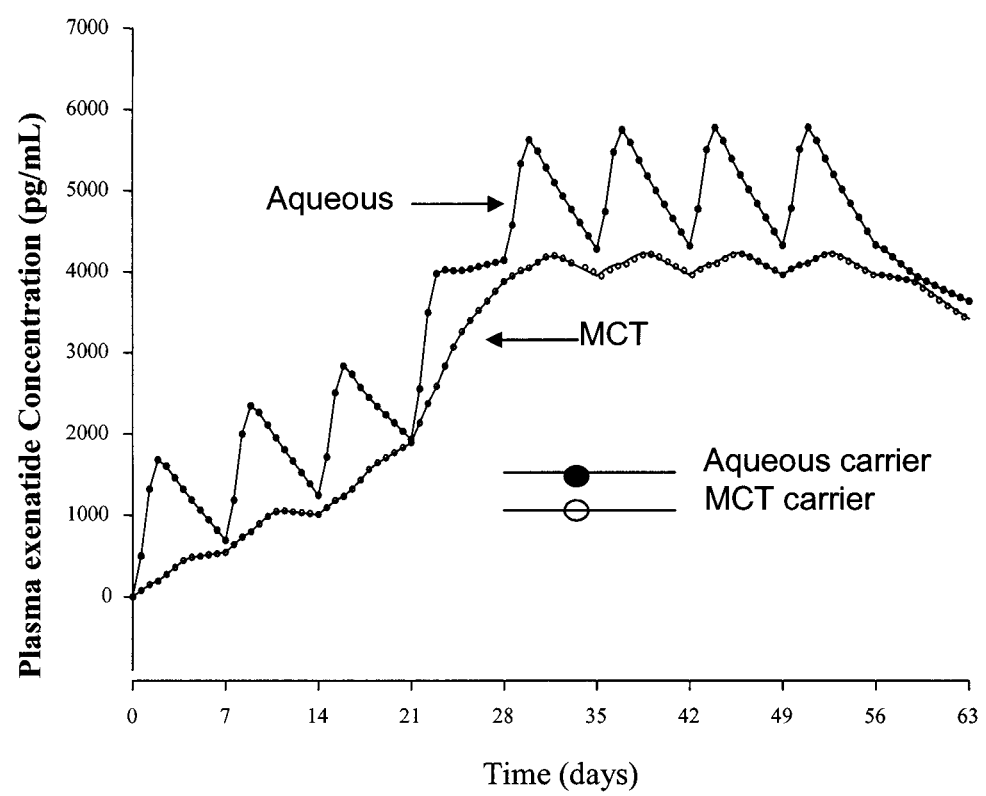
FIG. 2 is a graphical simulation (i.e., nanoparametric superposition) of data extrapolated from FIG. 1 of the plasma exenatide concentration over time for the microsphere formulation comprising the oil carrier and the microsphere formulation comprising the aqueous carrier in male Sprague Dawley Rats. The plasma concentration plateau of exenatide may be reached after about 5 dosings.

FIG. 2 is a graphical simulation of data extrapolated from FIG. 1 of the plasma exenatide concentration over time of the formulation comprising the MCT oil carrier and the comparative formulation comprising the aqueous carrier. The plasma concentration plateau of exenatide may be reached after about 5 dosings.

Example 4

A formulation comprising the microspheres of Example 1 in an aqueous carrier and a formulation comprising the microspheres of Example 1 in an MCT carrier were prepared. The burst release was evaluated by adding about 0.75 mL of the formulations to a 10 mM HEPES release buffer. The mixture was agitated to ensure that the microspheres achieved full contact with the HEPES release buffer. After incubation at 37° C. for one hour, the mixture was centrifuged and the aqueous phase was analyzed by HPLC to determine the burst release. The concentration of the dose tested for release was 150 mg/mL.

Figure 3:
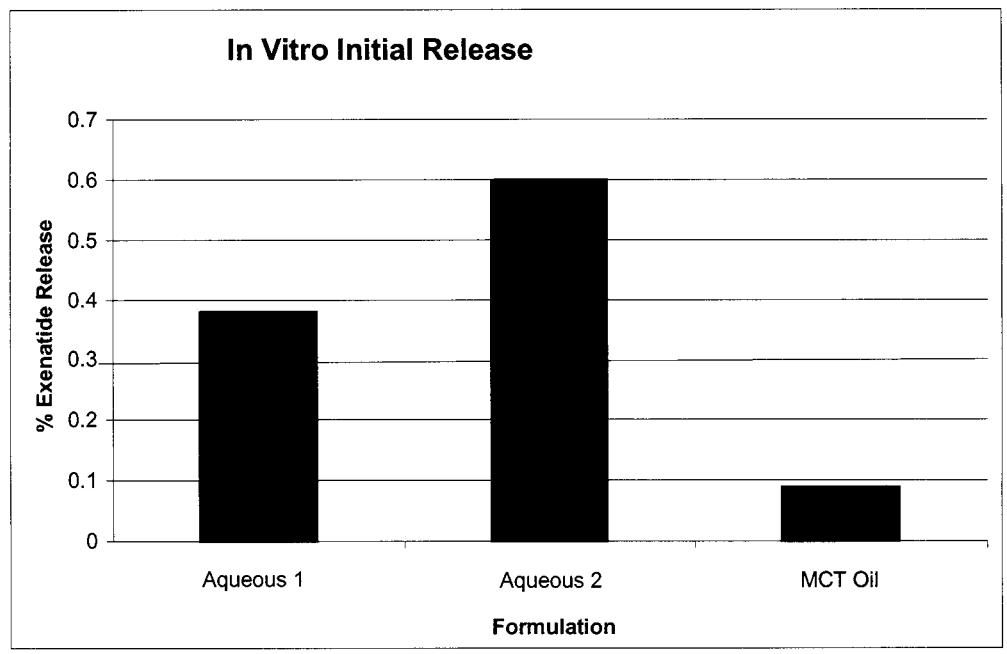
FIG. 3 illustrates the in vitro release for a formulation comprising microspheres in an oil carrier compared to formulations comprising microspheres in an aqueous carrier.

FIG. 3 shows the lower burst release of the formulation having the oil carrier compared to the formulations having an aqueous carrier. The graph shows that with an aqueous carrier, about 0.6% of exenatide was released in the burst. With the formulation having the MCT oil carrier, less than 0.1% of exenatide was released in the burst.

Figure 4:
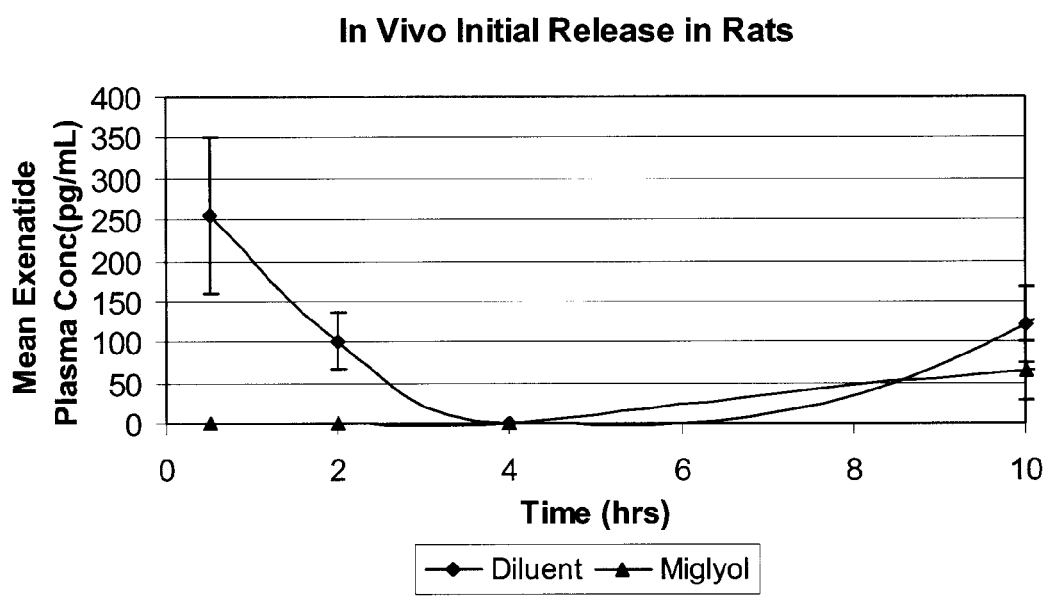
FIG. 4 illustrates the in vivo release profile in rats over 10 hours for a formulation comprising microspheres in an oil carrier and a formulation comprising microspheres in an aqueous carrier.

FIG. 4 illustrates the in vivo release profile in rats over 10 hours for the formulation of Example 1 in MCT oil compared to a formulation comprising the same microspheres in an aqueous (saline) carrier. In the time period following subcutaneous administration of the formulation, the entrance of exenatide into the plasma was markedly lower than the same microspheres administered in the aqueous carrier. The formulation of the invention shows no burst release, and a markedly more gradual entrance into the blood plasma versus the aqueous formulation. In contrast, the aqueous formulation showed a burst release followed by a sharper entrance into the blood plasma.

Example 5

Microparticles were prepared in a manner similar to that described in the examples in U.S. Pat. No. 5,439,688, the disclosure of which is incorporated by reference herein. Eight samples were prepared by briefly mixing an active pharmaceutical ingredient (i.e., davalintide, pramlintide, metreleptin, bovine serum albumin, sodium salicylate, salicylic acid, minocycline HCl, insulin) and polymer (i.e, poly(lactide-co-glycolide) copolymer or polycaprolactone/PLGA copolymer) and then the mixture was placed in a grinder to obtain a well-homogenized powder. Mixtures ranged from 2% to 10% w/w of the active pharmaceutical ingredient. The mixed powder was transferred to an extruder where the temperature was adjusted according to the chosen polymer. Some polymers needed higher temperatures to produce a melt with good flow properties. The extruder contained twin screws that moved clockwise to produce efficient mixing. The material was extruded through a 1.5 mm orifice, collected, cooled at room temperature, and cut into short strands about 1-2 inches long. These strands were then fed into a 12-tooth rotor mill, followed by a sieving step to produce microparticles of about 20 to 100 microns. The microparticles were collected and stored at 5° C. until further use.

Experimental samples were prepared by dispersing about 50 mg of the microparticles into 0.75 mL of a MCT oil carrier. The samples were stored at 5° C. and 25° C. for two days, two weeks, or one month, at which times representative samples were tested. The fraction of drug that remained in the microparticles and the fraction of drug that partitioned into the MCT oil carrier were determined. Briefly, the samples were centrifuged to separate the microparticles from the MCT oil carrier. Each portion was treated independently to determine the amount of drug it contained. Results are reported on the basis of the percent residing in each independent portion.

TABLE 4

PLGA copolymer; 2 Days Storage at 5° C.

| Compound | Microparticles | MCT Carrier |
| --- | --- | --- |
| davalintide | 99.8% | 0.2% |
| pramlintide | 100.0% | 0.0% |
| metreleptin | 100.0% | 0.0% |
| bovine serum albumin | 100.0% | 0.0% |
| sodium salicylate | 99.5% | 0.5% |
| salicylic acid | 98.9% | 1.1% |
| minocycline | 99.1% | 0.9% |

TABLE 5

PLGA copolymer; 1 Month Storage at 5° C.

| Compound | Microparticles | MCT Carrier |
| --- | --- | --- |
| davalintide | 99.4% | 0.6% |
| pramlintide | 99.7% | 0.3% |
| metreleptin | 100.0% | 0.0% |
| bovine serum albumin | 100.0% | 0.0% |
| sodium salicylate | 98.7% | 1.3% |
| salicylic acid | 99.9% | 0.1% |
| minocycline | 99.9% | 0.1% |
| insulin | 99.5% | 0.5% |

TABLE 6

PLGA copolymer; 2 Days Storage at 25° C.

| Compound | Microparticles | MCT Carrier |
| --- | --- | --- |
| davalintide | 100.0% | 0.0% |
| pramlintide | 100.0% | 0.0% |
| metreleptin | 100.0% | 0.0% |
| bovine serum albumin | 100.0% | 0.0% |
| sodium salicylate | 97.7% | 2.3% |
| salicylic acid | 99.1% | 0.9% |
| minocycline | 99.4% | 0.6% |

TABLE 7

PLGA copolymer; 1 Month Storage at 25° C.
PLGA Polymer; 1 Month Storage at 25° C.

| Compound | Microparticles | MCT Carrier |
| --- | --- | --- |
| davalintide | 100.0% | 0.0% |
| pramlintide | 100.0% | 0.0% |
| metreleptin | 100.0% | 0.0% |
| bovine serum albumin | 100.0% | 0.0% |
| sodium salicylate | 98.5% | 1.5% |
| salicylic acid | 99.8% | 0.2% |
| minocycline | 99.6% | 0.4% |
| insulin | 99.3% | 0.7% |

TABLE: 8 polycaprolactone/PLGA copolymer; Two Weeks Storage

| Compound | 5° C. | | 25° C. | |
| --- | --- | --- | --- | --- |
| | Microparticles | MCT Carrier | Microparticles | MCT Carrier |
| pramlintide | 100.0% | 0.0% | 100.0% | 0.0% |

The data in Tables 4-8 illustrate the broad applicability of the sustained release formulations described herein to a variety of different active pharmaceutical ingredients, including peptides and small molecules. The compositions have been successfully produced using a variety of peptides, bovine serum albumin, and even a selection of small molecules. Surprisingly salicylic acid, which is oil soluble, did not migrate into the MCT carrier oil, despite that its solubility in the MCT oil is greater than 30 mg/ml. Thus, the microparticles remain intact upon storage in MCT even when the active pharmaceutical ingredient is soluble in MCT. The data further illustrate that the compositions can be successfully produced even using other polymer mixtures in the microparticles.

Example 6

The percentage purity of exenatide was measured by HPLC at one month intervals over a 9 month period in the following four formulations: (i) a formulation comprising the microspheres of Example 1 stored in an oil MCT oil carrier at 5° C.; (ii) a formulation comprising the microspheres of Example 1 stored in an MCT oil carrier at 25° C.; (iii) dry microspheres of Example 1 that had been stored in a container for 9 months at 5° C. without a liquid carrier, and that were then admixed with an aqueous carrier immediately prior to the study; and (iv) dry microspheres of Example 1 that had been stored in a container for 9 months at 25° C. without a liquid carrier, and that were then admixed with an aqueous carrier immediately prior to the study.

Figure 5A:
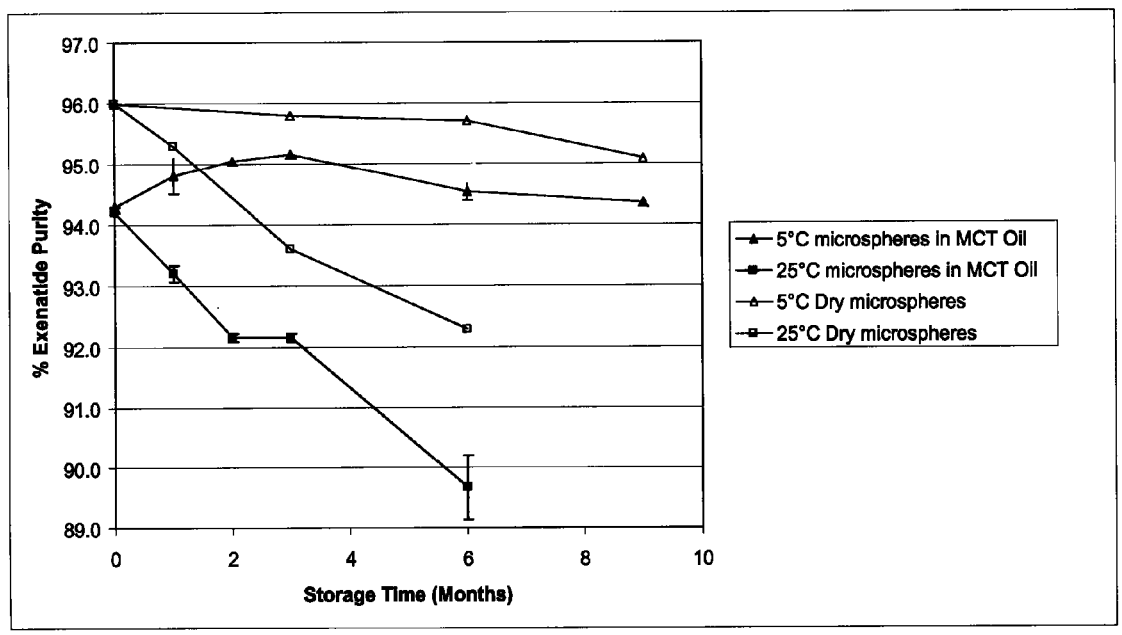
FIGS. 5A and B illustrate the purity of exenatide over 9 months at temperatures of 5° C. and 6 months at 25° C. when stored in the formulations comprising the microspheres of Example 1 with an oil carrier as compared to the purity of exenatide that was stored in dry microspheres of Example 1.
Figure 5B:
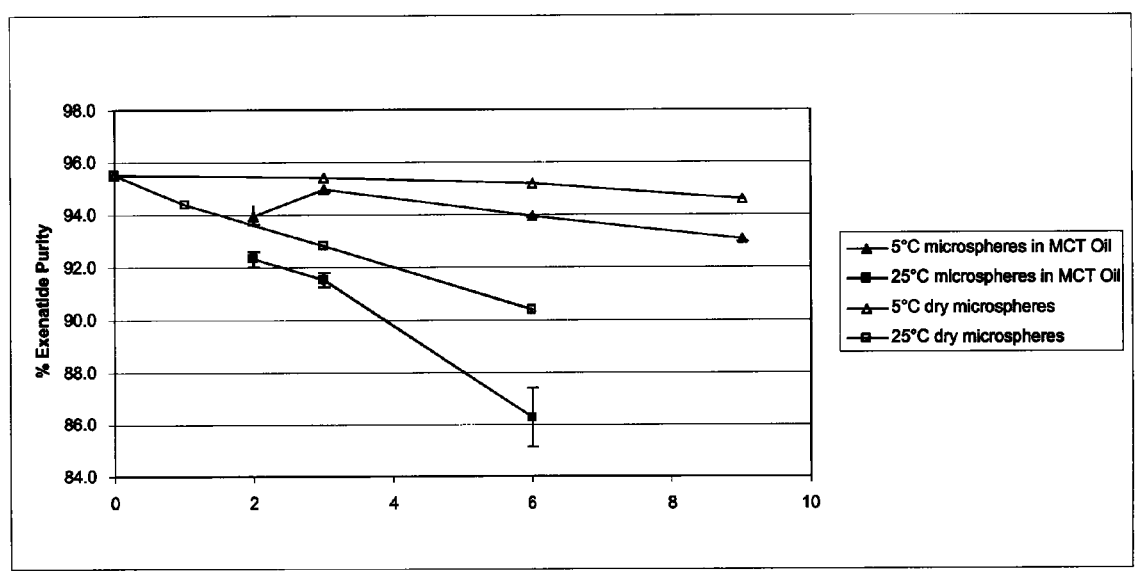
In FIG. 5B, the purity of exenatide was determined by reverse-phase HPLC.

FIGS. 5A and B show the following: (i) exenatide had a purity greater than 93% at 6 months and 9 months in the formulation with the oil carrier at a temperature of 5° C.; (ii) exenatide had a purity greater than 86% at 6 months and 9 months in the formulation with the oil carrier at a temperature of 25° C.; (iii) exenatide had a purity of greater than 94% at 6 months where the microspheres had been stored dry at 5° C.; and (iv) exenatide had a purity of greater than 90% at 6 months in the formulation where the microspheres had been stored dry at a temperature of 25° C. In FIG. 5A, the purity of exenatide was determined by strong cation exchange HPLC. In FIG. 5B, the purity of exenatide was determined by reverse-phase HPLC.

Example 7

Figure 6:
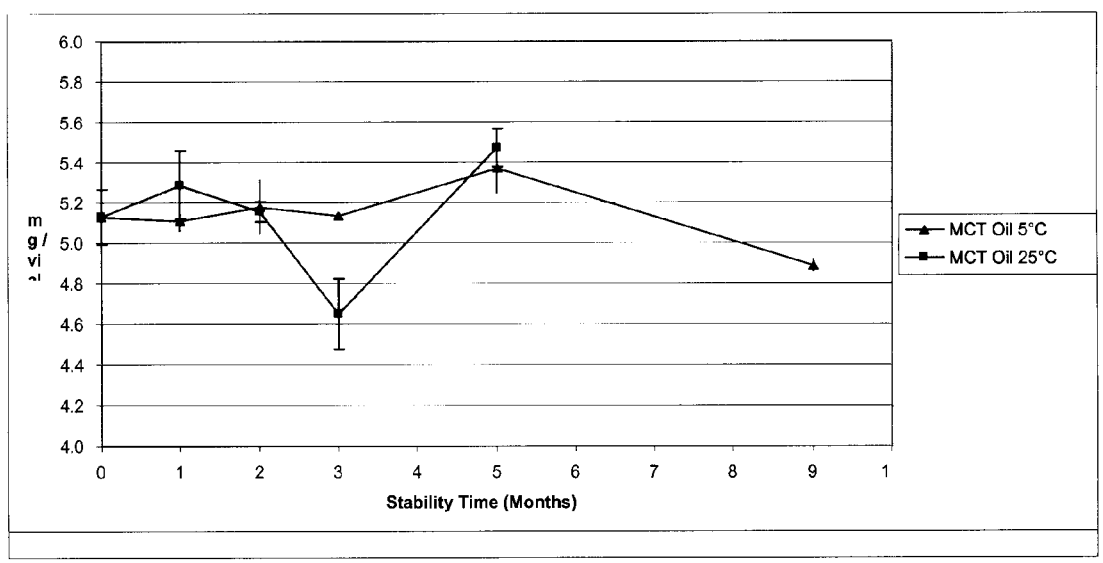
FIG. 6 illustrates the stability/potency of exenatide in a formulation where the microspheres are suspended in an oil carrier, where one formulation is stored at 5° C. and one formulation is stored at 25° C.

Formulations containing the microspheres from Example 1 and an MCT oil carrier were stored at 5° and the potency of exenatide was measured at monthly intervals for 9 months. Additionally, formulations containing the microspheres from Example 1 and an MCT oil carrier were stored at 25° and the potency of exenatide was measured at monthly intervals for 6 months. FIG. 6 presents the results which show that the potency of exenatide was preserved for at least 9 months.

Example 8

The physical integrity of a formulation containing the microspheres from Example 1 in an MCT oil carrier was analyzed. After storage for a period of 6 months at 5° C., the molecular weight of the poly(lactide-co-glycolide) copolymer did not change relative to time zero. After storage for a period of 6 months at 25° C., the molecular weight of the poly(lactide-co-glycolide) copolymer decreased by 6 kDaltons, which was comparable to the molecular weight change of dry microspheres (i.e., microspheres stored for 6 months at 25° C. not in any carrier). The mean diameter of the microspheres was measured after storage at 3, 6, and 9 months at either 5° C. or 25° C., and no change in mean diameter was detected relative to time zero.

Example 9

The ratio of lactide/glycolide for the microparticles was also investigated for use with various APIs. The Table below provides the various lactide/glycolide ratios used.

| Polymer | Drug | Approx polymer MW (kDa) | Lactide/Glycolide ratio for PLGA |
| --- | --- | --- | --- |
| PLGA | davalintide | 10 | 50/50 |
| PLGA | pramlintide | 10 | 50/50 |
| PLGA | Leptin | 10 | 75/25 |
| PLGA | BSA | 25 | 50/50 |
| PLGA | Na Salicylate | 25 | 50/50 |
| PLGA | Salicylic acid | 25 | 50/50 |
| PLGA | Minocycline | 10 | 75/25 |
| PLGA | Insulin | 25 | 50/50 |
| 1.1:1 PCL/PLGA | pramlintide | PCL = 150 PLGA = 10 | 50/50 |

All publications and patents are incorporated by reference herein. The foregoing has been described in detail, and the skilled artisan will recognize that modifications may be made without departing from the spirit or scope of the disclosure or appended claims.

What is claimed is:

1. A manufactured pre-mixed formulation for injection comprising a suspension of (i) a pharmaceutically acceptable non-aqueous carrier comprising one or more triglycerides and (ii) microspheres which comprise a biocompatible, biodegradable polymer and an active pharmaceutical ingredient, and wherein the pharmaceutically acceptable non-aqueous carrier comprises from 0 to 2 wt % of $C_6$ fatty acid, from 50 to 65 wt % of $C_8$ fatty acid, from 30 to 45 wt % of $C_{10}$ fatty acid, and form 0 to 2 wt % of $C_{12}$ fatty acid based on the total fatty acid content of the one or more triglycerides.

2. The formulation of claim 1, further comprising a pharmaceutically acceptable excipient.

3. The formulation of claim 2, wherein the pharmaceutically acceptable excipient is a sugar, or a sugar alcohol, and the formulation further comprises an antioxidant, or a preservative, or a combination of two or more thereof.

4. The formulation of claim 2, wherein the pharmaceutically acceptable excipient is sucrose, glucose, dextrose, galactose, maltose, trehalose, fructose, maltodextrin, glycol, glycerol, erythritol, threitol, arabitol, ribitol, sorbitol, dulcitol, iditol, isomalt, maltitol, lactitol, mannitol, xylitol, benzoic acid, sorbic acid, meta cresol, sodium benzoate, potassium sorbate, methylparaben, propylparaben, butylparaben, benzalkonium chloride, sodium metabisulfite, butylated hydroxy anisole, butylated hydroxy toluene, sodium sulfite, tocopherol, thymol, ascorbate, propyl gallate, or a combination of two or more thereof.

5. The formulation of claim 1, wherein the formulation does not further comprise a gel-forming agent.

6. The formulation of claim 1, wherein the biocompatible, biodegradable polymer is a polylactide, a copolymer of a polylactide, a polyglycolide, a copolymer of a polyglycolide, a poly(lactide-co-glycolide) copolymer, a polylactic acid, a copolymer of a polylactic acid, a polyglycolic acid, a copolymer of a polyglycolic acid, a poly(lactic acid-co-glycolic acid) copolymer, a polycaprolactone, a copolymer of a polycaprolactone, a polycarbonate, a copolymer of a polycarbonate, a polyesteramide, a copolymer of a polyesteramide, a polyanhydride, a copolymer of a polyanhydride, a polyamino acid, a copolymer of a polyamino acid, a polyorthoester, a copolymer of a polyorthoester, a polycyanoacrylate, a copolymer of a polycyanoacrylate, a poly(p-dioxanone), a copolymer of a poly(p-dioxanone), a polyalkylene oxalate, a copolymer of a polyalkylene oxalate, a polyurethane, a copolymer of a polyurethane, or a combination of two or more thereof.

7. The formulation of claim 1, wherein the active pharmaceutical ingredient is a GLP-1 receptor agonist, GLP-1(7-37), GLP-1(7-36)-NH$_2$, exenatide, pramlintide, davalintide, Val$^{27}$-davalintide, metreleptin, insulin, glucagon agonist, glucagon antagonist, a chimera of a GLP-1 receptor agonist and a glucagon agonist, bovine serum albumin, sodium salicylate, salicylic acid, minocycline HCl, insulin, or a small molecule organic compound.

8. The formulation of claim 1, wherein the microspheres are present in the formulation at a concentration of from 10 mg/ml to 500 mg/ml or from 20 mg/ml to 200 mg/ml.

9. A method for treating diabetes, stimulating insulin release; lowering plasma glucagon; reducing food intake; reducing appetite; decreasing gastric motility; delaying gastric emptying; lowering plasma lipid levels; treating impaired glucose tolerance; treating hyperglycemia; treating obesity; treating overweight; treating fatty liver disease; or treating non-alcoholic steatohepatitis in a patient in need thereof comprising administering to the patient the formulation of claim 1.

10. The method of claim 9, further comprising administering to the patient metformin, a sulfonylurea, a thiazolidinedione, or a combination of two or more thereof.

11. A kit comprising a container which comprises the formulation of claim 1 and instructions for use.

12. The kit of claim 11, wherein the container is a single-dose or multi-dose pen injector, single-dose or multi-dose vial, or single-dose or multi-dose cartridge.

13. A manufactured pre-mixed formulation for injection comprising a suspension of:
(i) a pharmaceutically acceptable non-aqueous carrier comprising one or more triglycerides, wherein the carrier comprises from 0 to 2 wt % of C$_6$ fatty acid, from 50 to 65 wt % of C$_8$ fatty acid, from 30 to 45 wt % of C$_{10}$ fatty acid, and from 0 to 2 wt % of C$_{12}$ fatty acid based on the total fatty acid content of the one or more triglycerides; and
(ii) microspheres comprising a poly(lactide-co-glycolide) polymer, about 2 wt % of sucrose; and about 5 wt % of exenatide as the active pharmaceutical ingredient, and wherein the ratio of lactide:glycolide in the polymer is about 1:1.

14. The manufactured pre-mixed formulation for injection of claim 6, wherein the biocompatible, biodegradable polymer is the poly(lactide-co-glycolide) polymer, wherein the ratio of lactide:glycolide in the polymer is about 1:1.

15. The manufactured pre-mixed formulation for injection of claim 7, wherein the active pharmaceutical ingredient is exenatide.

16. The manufactured pre-mixed formulation for injection of claim 15, wherein the exenatide is present in the microspheres in an amount of about 5 wt %.

17. The manufactured pre-mixed formulation for injection of claim 4, wherein the pharmaceutically acceptable excipient is sucrose.

18. The manufactured pre-mixed formulation for injection of claim 2, wherein the pharmaceutically acceptable excipient is sucrose; the biocompatible, biodegradable polymer is a poly(lactide-co-glycolide) polymer; the active pharmaceutical ingredient is exenatide.

* * * * *